(12) United States Patent
Fujita et al.

(10) Patent No.: US 8,513,961 B2
(45) Date of Patent: *Aug. 20, 2013

(54) DETECTION METHOD FOR DEFECT OF SENSOR

(75) Inventors: Tomohisa Fujita, Aichi (JP); Takeshi Kawai, Aichi (JP); Satoshi Teramoto, Aichi (JP); Shigeki Mori, Gifu (JP)

(73) Assignee: NGK Spark Plug Co., Ltd. (JP)

( * ) Notice: Subject to any disclaimer, the term of this patent is extended or adjusted under 35 U.S.C. 154(b) by 686 days.

This patent is subject to a terminal disclaimer.

(21) Appl. No.: 12/688,956

(22) Filed: Jan. 18, 2010

(65) Prior Publication Data

US 2010/0225339 A1 Sep. 9, 2010

(30) Foreign Application Priority Data

Jan. 19, 2009 (JP) ................................. 2009-008506

(51) Int. Cl.
*G01R 27/08* (2006.01)
(52) U.S. Cl.
USPC ......... 324/693; 73/23.31; 73/31.05; 204/424; 204/428

(58) Field of Classification Search
USPC .................... 73/23.31, 31.05; 204/424–428, 204/431; 324/699
See application file for complete search history.

(56) References Cited

U.S. PATENT DOCUMENTS

| | | | | | |
|---|---|---|---|---|---|
| 4,310,401 | A | * | 1/1982 | Stahl | 204/428 |
| 5,039,972 | A | * | 8/1991 | Kato et al. | 338/34 |
| 5,467,636 | A | * | 11/1995 | Thompson et al. | 73/23.31 |
| 7,311,093 | B2 | * | 12/2007 | Hayashi et al. | 123/688 |
| 2004/0069629 | A1 | * | 4/2004 | Tanaka et al. | 204/424 |
| 2004/0221641 | A1 | * | 11/2004 | Moritsugu et al. | 73/23.31 |
| 2008/0121020 | A1 | * | 5/2008 | Oya et al. | 73/31.05 |

FOREIGN PATENT DOCUMENTS

JP 2006030140 2/2006

* cited by examiner

*Primary Examiner* — Hezron E Williams
*Assistant Examiner* — Hoang Nguyen
(74) *Attorney, Agent, or Firm* — Kusner & Jaffe

(57) ABSTRACT

A defect detection method for a sensor in which a fixing member provides a seal between a sensor element and tubular metallic members, the method being capable of detecting breakage of a conductor caused by breakage of the element.

9 Claims, 9 Drawing Sheets

PRIOR ART

DETECTION METHOD FOR DEFECT OF SENSOR

FIELD OF THE INVENTION

The present invention relates to a defect detection method for a sensor which includes a sensor element having a solid electrolyte layer and a pair of electrodes.

BACKGROUND OF THE INVENTION

An air-fuel-ratio sensor and an oxygen sensor, which detect the concentration of oxygen within exhaust gas, are known as gas sensors, and are used for improving the fuel consumption of internal combustion engines such as automotive engines and/or for performing combustion control for the engines. There has been a desire for a reduction in the amount of nitrogen oxides ($NO_x$) within exhaust gas in order to cope with the strengthened exhaust gas regulation for automobiles, and $NO_x$ sensors which can directly measure $NO_x$ concentration have been developed. Such a gas sensor includes a sensor element, and the concentration of a specific gas is detected on the basis of the output from the sensor element. A known structure of such a sensor element is such that the sensor element assumes a platelike shape and includes at least one cell composed of an oxygen-ion conductive solid electrolyte layer formed of zirconia or the like, and a pair of electrodes formed on the surface of the solid electrolyte layer.

FIG. 9 shows the structure of a gas sensor (hereinafter, may be simply referred to as a "sensor") 1000 which includes a plate-shaped sensor element 100. The sensor 1000 is an assembly into which the sensor element 100 is assembled. Sensor 1000 includes the sensor element 100, and a metallic shell 200 for mounting the sensor 1000 to an object (e.g., an exhaust pipe of an automotive engine). The metallic shell 200 assumes an approximately cylindrical shape and has an inner hole 280 formed therein. The metallic shell 200 holds the sensor element 100 within the inner hole 280 such that a front end portion (a detection portion 110) of the sensor element 100 projects from the metallic shell 200. The sensor element 100 is held within the metallic shell 200 via a collar unit 450. The collar unit 450 is fixed to the sensor element 100 at a predetermined position along the longitudinal direction of the sensor element 100. The collar unit 450 is brought into engagement with a step portion 290 provided in the inner hole 280 of the metallic shell 200. Notably, the collar unit 450 is composed of a tubular metallic cup 205 which has, at its front end, an abutment portion 215 for abutment against the step portion 290; a ceramic holder 210 accommodated within the metallic cup 205; and a first fixing member (specifically, powder of talc) 220 which is compressively charged into the metallic cup 205 to form a layer on the ceramic holder 210, to thereby provide a seal between the outer surface of the sensor element 100 and the inner surface of the metallic cup 205.

In a state where the collar unit 450 is engaged with the step portion 290, a second fixing member (specifically, powder of talc) 230 and a ceramic sleeve 300 are placed within the inner hole 280 so as to surround the sensor element 100. Subsequently, a rear end portion of the metallic shell 200 is crimpled radially inward, with a metallic packing 310 disposed between the rear end portion and the ceramic sleeve, so as to compress the charged second fixing member 230, to thereby hold (fix) the sensor element 100 within the metallic shell 200.

Further, in the gas sensor 1000, an outer sleeve 800 is joined to the outer circumference of a rear end portion of the metallic shell 200, and lead wires 680 connected to electrodes of the sensor element 100 via terminal electrodes extend outward from the rear end of the outer sleeve 800 via a grommet 770. Meanwhile, an outer protector 400 and an inner protector 410, which are formed of metal and which cover the detection portion 110 of the sensor element 100, are attached to the outer circumference of a front end portion of the metallic shell 200.

Since ceramic layers, such as solid electrolyte layers, which constitute the sensor element 100 are brittle, the sensor element 100 may crack or break at the time of assembly of the sensor 1000 or during shipment of the sensor 1000, whereby the sensor element becomes defective. In view of this, there has been proposed a method of detecting a defect of the sensor 1000 by means of introducing a pressurized gas into the sensor 1000. Further, a technique has been proposed in order to detect a growing crack of the sensor element 100. (See Japanese Patent Application Laid-Open (kokai) No. 2006-30140). The proposed technique makes use of a phenomenon that, if the sensor 1000 has a crack, a portion of the sensor 1000 displaces when the sensor 1000 is pressed, and detects the crack from a change rate of the pressing load of the sensor 1000.

In the case of the gas sensor 1000 configured such that the first and second fixing members 220 and 230 provide a seal against the outer surface of the sensor element 100 and a seal against the inner surfaces of the tubular metallic members (the metallic cup 215 and the metallic shell 200), even when a portion of the sensor element 100 surrounded by the first and second fixing members 220 and 230 breaks, detection of such a defect is difficult.

In general, when the sensor element 100 breaks, each of paired conductors, which are provided on a solid electrolyte layer and extend through the portion surrounded by the first and second fixing members 220 and 230, also breaks. Therefore, by means of detecting electrical discontinuity between the paired conductors, occurrence of breakage, such as two-piece breakage, of the sensor element 100 can be determined. However, in the portion of the sensor element 100 surrounded by the first and second fixing members 220 and 230, even when sensor element 100 breaks, the first and second fixing members 220 and 230 support the sensor element 100 through the close contact of fixing members 220 and 230 with the outer surface of the sensor element 100. Therefore, even when the sensor element 100 breaks, in some cases, no gap is formed between portions of the conductors physically separated from each other through the breakage, and contact therebetween is maintained. In such a case, the above-mentioned electrical discontinuity cannot be detected as a continuity defect. In some cases, such a defective sensor 1000 may be shipped and attached to an object to which the sensor is to be attached, such as an exhaust pipe, for use. In such a case, during use, the breakage of the conductors may become noticeable due to vibration, thermal expansions of members, or other causes, and a continuity defect may be discovered.

In view of the forgoing, an object of the present invention is to provide a defect detection method for a sensor in which a fixing member providing a seal between a sensor element and a tubular metallic member is disposed to surround the sensor element, the method being capable of detecting breakage of a conductor caused by, for example, two-piece breakage of the sensor element.

SUMMARY OF THE INVENTION

The present invention provides a defect detection method for a sensor comprising a sensor element which includes at least one cell having a solid electrolyte layer extending in an axial direction; a tubular metallic member which surrounds the circumference of the sensor element; and a fixing member which is in contact with an inner surface of the tubular metallic member and an outer surface of the sensor element and which provides a seal therebetween, the cell including a pair of conductors which are formed on the solid electrolyte layer such that the conductors extend through a portion of the sensor element that is surrounded by the fixing member. The method comprises heating the tubular metallic member so as to produce a difference in dimension attributable to a difference in rate of thermal expansion between the tubular metallic member and the fixing member and a difference in rate of thermal expansion between the tubular metallic member and the sensor element; and detecting breakage of the pair of conductors (i.e., determining whether or not the pair of conductors are broken) in a state where the difference in dimension is present.

The present method can reliably detect breakage of the conductors formed on the solid electrolyte layer, which breakage has been caused by breakage or the like of the sensor element, even when contact between portions of the conductors physically separated from each other because of the breakage is maintained by the fixing member that surrounds the sensor elements and which is in contact with the outer surface of the sensor element. That is, according to the defect detection method for a sensor of the present invention, as a result of forcedly producing the above-mentioned difference in dimension through heating of the tubular metallic member, the contact force (fixing force) of the fixing member against the sensor element is weakened so as to produce a gap or positional shift between portions of the conductors that are physically separated from each other because of element breakage or the like. By virtue of this procedure, when the conductors are broken, the breakage of the conductors can be detected in a state where the breakage has been made noticeable. Therefore, a defect caused by the element breakage or the like of the sensor can be detected reliably.

In the defect detection method for a sensor of the present invention, preferably, the heating of the tubular metallic member is performed by induction heating.

In this case, the tubular metallic member can be heated quickly, whereby the above-mentioned difference in dimension becomes larger, and the breakage of the conductors can be made more noticeable. Further, since substantially only the tubular metallic member can be heated selectively, a portion of the sensor which is located rearward of the tubular metallic member and which is relatively weak against heat can be prevented from deteriorating.

Further, in the defect detection method for a sensor of the present invention, the breakage of the pair of conductors may be detected within a period which follows completion of the heating of the tubular metallic member by the induction heating and in which the difference in dimension is present.

In this case, there can be prevented deterioration of the solid electrolyte layer, which deterioration would otherwise be caused by eddy current which flows within the solid electrolyte layer because of the induction heating.

In the case where the sensor element is configured such that a heater, including a heat generation resistor that extends in the axial direction is laminated on the cell, preferably, the solid electrolyte layer is heated through supply of electricity to the heat generation resistor, and the breakage of the pair of conductors is detected in a state where the solid electrolyte layer is heated.

In this case, the solid electrolyte layer can be stably activated (heated to an operation temperature or higher) through heating by the heater. Therefore, the breakage of the pair of conductors can be detected accurately by use of an output from a line which supplies electricity between the pair of conductors, in a state where the internal resistance of the solid electrolyte layer has been lowered.

Moreover, the defect detection method for a sensor of the present invention may be applied to the case where the sensor element is configured such that a heater extending in the axial direction is laminated on the cell, and the heater includes a heat generation resistor extending through the portion of the sensor element that is surrounded by the fixing member. In such a case, preferably, the method comprises heating the tubular metallic member so as to produce the above-mentioned difference in dimension; and detecting breakage of the heat generation resistor in a state where the difference in dimension is present.

In this case, in addition to breakage of the conductors of the solid electrolyte layer (cell), breakage of the heat generation resistor can be detected, whereby a defect of the heater can also be detected. Notably, when breakage of the conductors of the solid electrolyte layer and breakage of the heat generation resistor are to be detected, preferably, breakage of the heat generation resistor is first detected, and breakage of the conductors of the solid electrolyte layer is then detected, because this enables the detection of breakage of the conductors of the solid electrolyte layer to be performed in view of the heating failure caused by breakage of the heat generation resistor.

Notably, in the present invention, examples of the fixing member of the gas sensor include inorganic powder, such as powder of talc or powder of boron nitride, and glass (silicic acid compound such as silicic acid glass or silicate glass). The defect detection method for a sensor of the present invention is advantageously applied to a sensor which includes a fixing member composed of a compact which is formed through compressively charging inorganic powder between the inner surface of the tubular metallic member and the outer surface of the sensor element.

The fixing member composed of a compact formed through compressive charging of inorganic powder comes into contact (close contact) with the outer surface of the sensor element while pressing the outer surface. Therefore, even if breakage occurs at a portion of the sensor element surrounded by the fixing member, a gap is hardly formed between physically separated portions of the conductors or the heat generation resistor, because of pressing force (fixing force) from the fixing member. When the defect detection method for a sensor of the present invention is applied, even in such a state, a gap or positional shift is forcedly produced between the physically separated portions of the conductors or the heat generation resistor. Therefore, breakage of the conductors and the heat generation resistor can be detected accurately.

According to the present invention, breakage of the conductors on the solid electrolyte layer and breakage of the heat generation resistor of the heater, which occur in a portion of the sensor element that is surrounded by the fixing member due to breakage or the like of the sensor element, can be detected accurately.

DETAILED DESCRIPTION OF PREFERRED EMBODIMENTS

Figure 1:
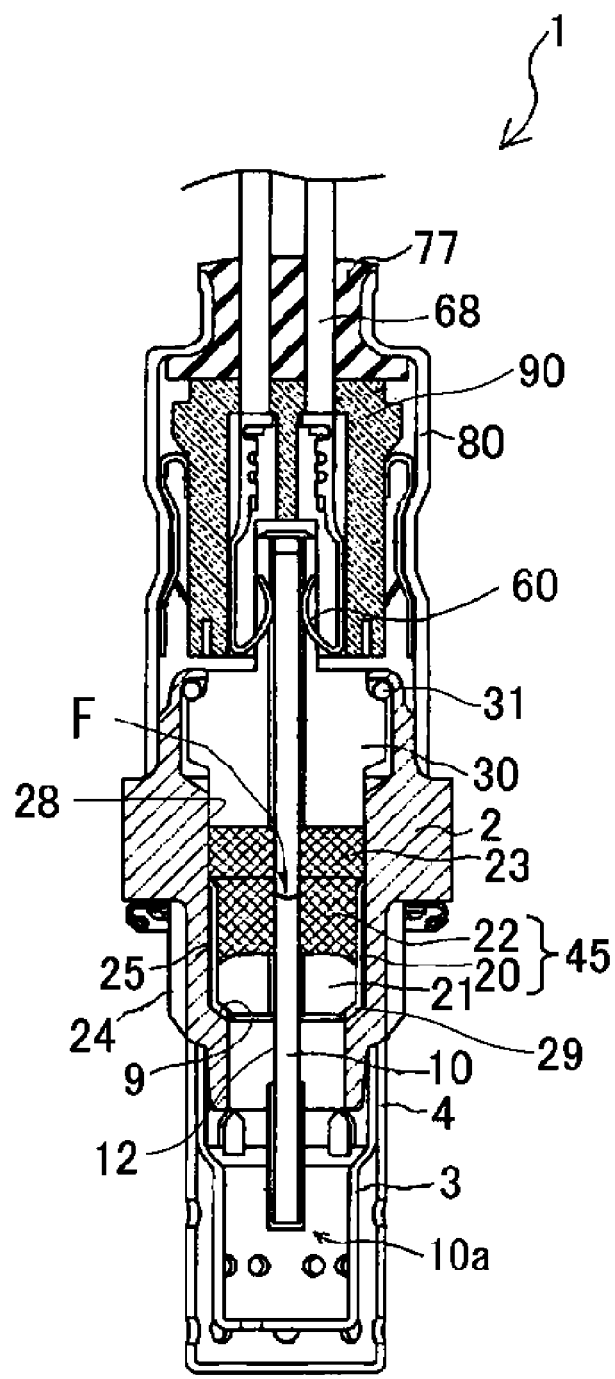
FIG. 1 is an overall cross sectional view of a sensor (an oxygen sensor) 1 according to an embodiment, taken along the longitudinal direction thereof.

Referring now to the drawings wherein the showings are for the purpose of illustrating the preferred embodiment of the invention only, and not for the purpose of limiting same, FIG. 1 shows a longitudinal cross sectional view of a sensor (oxygen sensor) 1, for which the defect detection method for a sensor of the present invention is preferably used. Notably, the lower side of FIG. 1 will be referred to as "front end" side, and the upper side thereof will be referred to as "rear end" side.

The sensor (oxygen sensor) 1 is an assembly in which a sensor element 10 is assembled to a metallic shell 2 and an outer sleeve 80. The sensor 1 includes the sensor element 10, which assumes a platelike shape, and the metallic shell 2, which is mounted onto an exhaust pipe of an automotive engine. The metallic shell 2 assumes an approximately cylindrical, tubular shape. The metallic shell 2 has a thread portion 24, which is formed on the outer surface of the metallic shell 2 and is used to fix the sensor 1 to the exhaust pipe. Meanwhile, the metallic shell 2 has an inner hole 28, and has a step portion 9 on the front end side. The step portion 9 projects radially inward from the wall surface 25 of the inner hole 28. The metallic shell 2 holds the sensor element 10 in the inner hole 28 such that a front end portion (detection portion 10a) of the sensor element 10 projects from the front end of the metallic shell 2.

The sensor element 10 is held within the metallic shell 2 via a collar unit 45. The collar unit 45 is fixed to the sensor element 10 at a predetermined position along the longitudinal direction of the sensor element 10. The collar unit 45 is brought into engagement with the step portion 9 provided in the inner hole 28 of the metallic shell 2. Notably, the collar unit 45 is composed of a tubular metallic cup 20 which has, at its front end, an abutment portion 29 for abutment against the step portion 9; a ceramic holder 21 accommodated within the metallic cup 20; and a first fixing member 22 which is composed of inorganic powder which is compressively charged into the metallic cup 20 to form a layer on the ceramic holder 21. In a state where the abutment portion 29 of the collar unit 45 is engaged with the step portion 9, a second fixing member 23 formed of inorganic powder and a ceramic sleeve 30 are placed within the inner hole 28 to surround the sensor element 10. Subsequently, a rear end portion of the metallic shell 2 is crimpled radially inward, with a metallic packing 31 disposed between the rear end portion and the ceramic sleeve 30, so as to compress the charged second fixing member 23, to thereby fixedly hold the sensor element 10 within the metallic shell 2. The first fixing member 22 is in contact (close contact) with the outer surface 12 of the sensor element 10 and the inner surface of the metallic cup 20 to thereby provide a seal therebetween. Further, the second fixing member 23 is in contact (close contact) with the outer surface 12 of the sensor element 10 and the inner surface 25 of the metallic shell 2 to thereby provide a seal therebetween.

Further, the outer sleeve 80 is joined to the outer circumference of a rear end portion of the metallic shell 2, and lead wires 68 connected to electrodes of the sensor element 10 via metallic terminals 60 extend outwardly from the rear end of the outer sleeve 80 via a grommet 77. The metallic terminals 60 are connected to ends of the lead wires 68, whereby the lead wires 68 are electrically connected to electrode terminals (not shown) provided at the rear end of the gas sensor element 10. The metallic terminals 60 are accommodated within an insulating ceramic separator 90 held within the outer sleeve 80. Meanwhile, an outer protector 4 and an inner protector 3, which are formed of meal and which have gas introduction holes, are attached to the outer circumference of a front end portion of the metallic shell 2 such that the outer protector 4 and the inner protector 3 cover the detection portion 10a of the sensor element 10.

Notably, in the present embodiment, each of the first and second fixing members 22 and 23 is a compact formed through compressive charging of powder of talc, which is inorganic powder. The first and second fixing members 22 and 23 correspond to the "fixing member" in the claims. Meanwhile, the ceramic holder 21 and the ceramic sleeve 30 in the present embodiment do not correspond to the "fixing member" because of the following reason. Although the ceramic holder 21 and the ceramic sleeve 30 serve as a guide for positioning the sensor element 10, which is passed through their center holes, they do not have a function of applying pressing force to the outer surface 12 of the sensor element 10 (in other words, coming into close contact with the outer surface 12 of the sensor element 10), to thereby fix the sensor element 10. Further, the metallic cup 20 in contact with the first fixing member 22 and the metallic shell 2 in contact with the second fixing member 23 each correspond to the "tubular metallic member" in the claims.

Notably, the first and second fixing members 22 and 23 are not limited to those formed of powder of talc. Ceramic powder, such as powder of boron nitride or powder of cordierite, can be used, and a powder mixture thereof can be used. Further, the fixing member is not limited to a compact formed through compressively charging these powders, and may be a seal member formed through melting and solidified glass (silicic acid compound such as silicic acid glass or silicate glass).

In the case where the gas sensor 1 is normal, naturally, the sensor element 10 is not broken. However, in some cases, as shown in FIG. 1, the sensor element 10 breaks at the center with respect to the longitudinal direction, whereby a fractured portion F may be produced (breakage of conductors may occur). The fractured portion F is present in a portion of the sensor element 10 surrounded by the first fixing member 22. However, since the first fixing member 22 presses the sensor element 10 from the outside and fixes the sensor element 10, portions of the conductors which are physically separated at the fractured portion F are in close contact with each other and maintain continuity therebetween, whereby breakage of the conductors is not noticeable.

Next, the structure of the sensor element (oxygen sensor element) 10 will be described with reference to an exploded perspective view of FIG. 2. The sensor element 10 assumes the form of an elongated plate, and is composed of a sensor portion 19 capable of detecting oxygen concentration, and a heater 14 capable of heating the sensor portion 19, which portions are laminated together. The sensor portion 19 includes an oxygen concentration cell 12 and an oxygen pump cell 13.

Notably, since a method (operation) of oxygen detection by the oxygen concentration cell 12 and the oxygen pump cell 13 is the same as that of a known oxygen sensor, its description will be not repeated.

Figure 2:
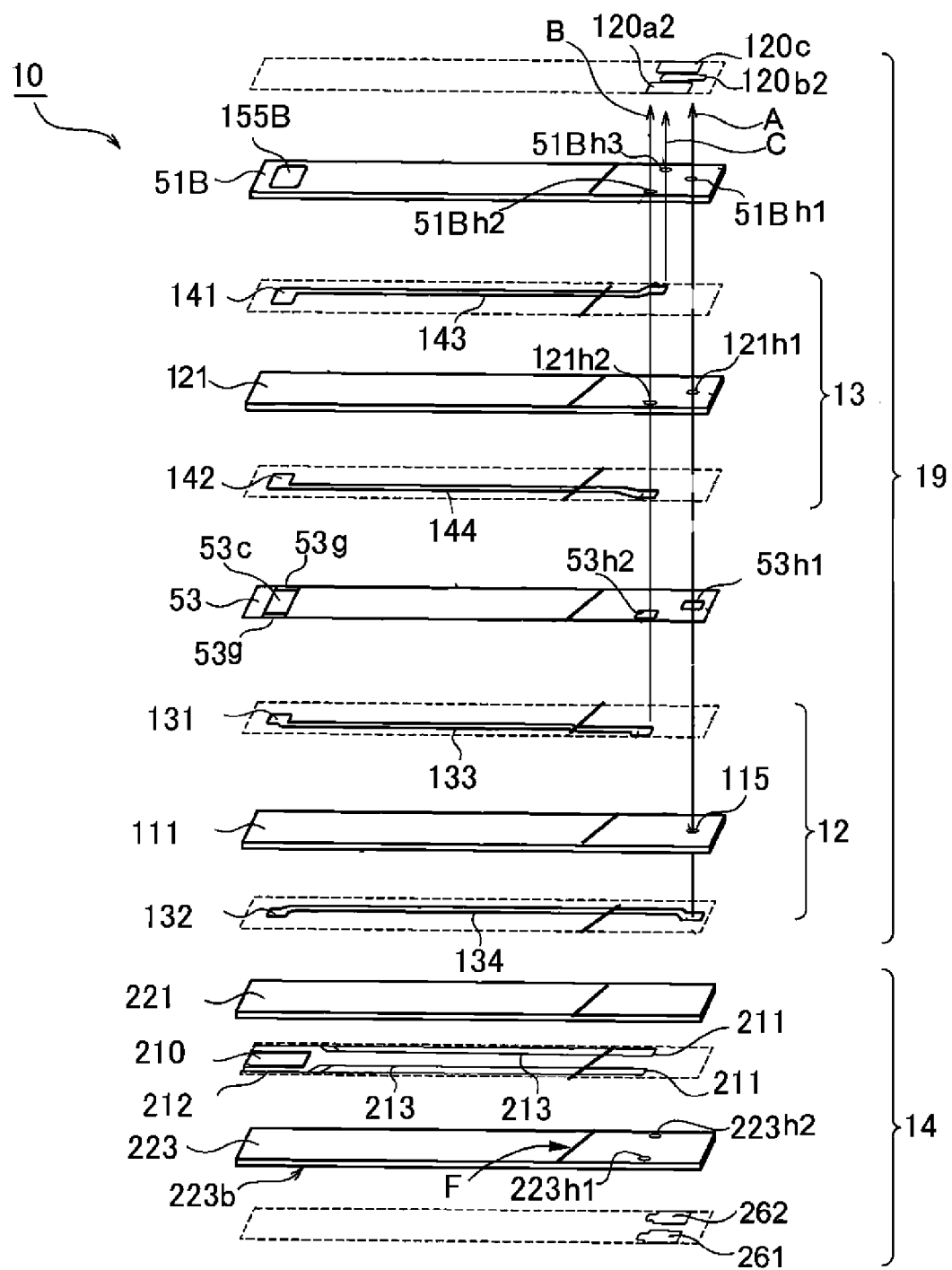
FIG. 2 is an exploded perspective view showing the structure of a sensor element 10.

As shown in FIG. 2, the oxygen concentration cell 12 includes a first solid electrolyte layer 111 formed of a partially stabilized zirconia sintered body, and a detection electrode 131 and a reference electrode 132 formed on the front and back surfaces, respectively, of the first solid electrolyte layer 111 on the front end side thereof such that they face each other. A first lead portion 133 extends from the detection electrode 131 toward the base end in the longitudinal direction. Further, a second lead portion 134 extends from the reference electrode 132 toward the base end in the longitudinal direction.

An insulating layer 53 mainly formed of alumina is stacked on the upper surface of the oxygen concentration cell 12. A rectangular gas measurement chamber 53c is formed in the insulating layer 53 on the front end side thereof, and the detection electrode 131 is exposed to the interior of the gas measurement chamber 53c. Diffusion resistance portions 53g are provided at opposite sides of the circumferential edge of the gas measurement chamber 53c, the sides extending in the longitudinal direction of the insulating layer 53. Thus, a gas to be detected is introduced into the gas measurement chamber 53c via, i.e., through, the diffusion resistance portions 53g.

Further, a through-hole 115 is formed in a rear end portion of the first solid electrolyte layer 111 at a position coinciding with a through-hole line A. Similarly, through-holes 53h1 and 53h2 are formed in a rear end portion of the insulating layer 53 at a position coinciding with the through-hole line A and at a position coinciding with a through-hole line B, respectively.

Next, an oxygen pump cell 13 will be described.

The oxygen pump cell 13 includes a second solid electrolyte layer 121 formed of a partially stabilized zirconia sintered body, and a third electrode 141 and a fourth electrode 142 formed on the front and back surfaces, respectively, of the second solid electrolyte layer 121 on the front end side thereof such that they face each other. A third lead portion 143 extends from the third electrode 141 toward the base end in the longitudinal direction. Further, a fourth lead portion 144 extends from the fourth electrode 142 toward the base end in the longitudinal direction.

The fourth electrode 142 is exposed to the interior of the gas measurement chamber 53c of the insulating layer 53 located under the oxygen pump cell 13.

An insulating layer 51B mainly formed of alumina is stacked on the oxygen pump cell 13. A rectangular cutout is formed in a front end portion of the insulating layer 51B, and a porous protection layer 155B is disposed in the rectangular cutout to cover the third electrode 141. The porous protection layer 155B suppresses poisoning of the third electrode 141.

The oxygen pump cell 13 having the above-described configuration pumps oxygen within the gas measurement chamber 53c by use of the third electrode 141 and the fourth electrode 142.

Meanwhile, through-holes 121h1 and 121h2 are formed in a base end portion of the second solid electrolyte layer 121 at positions coinciding with the through-hole lines A and B, respectively.

Further, through-holes 51Bh1, 51Bh2, and 51Bh3 are formed in a base end portion of the insulating layer 51B at a position coinciding with the through-hole line A, a position coinciding with the through-hole line B, and a position coinciding with a through-hole line C, respectively.

A conductor (not shown) formed along the through-hole line A forms an electrical path which extends from the reference electrode 132 to an electrode terminal 120b2 formed on the uppermost insulating layer 51B. Similarly, a conductor (not shown) formed along the through-hole line B forms an electrical path which extends from the detection electrode 131 and the fourth electrode 142 to an electrode terminal 120a2 formed on the uppermost insulating layer 51B. Further, a conductor (not shown) formed along the through-hole line C forms an electrical path which extends from the third electrode 141 to an electrode terminal 120c formed on the uppermost insulating layer 51B.

Next, the heater 14 will be described. The heater 14 includes insulating layers 221 and 223 mainly formed of alumina, a heat generation resistor 210 sandwiched therebetween, and a pair of external connection pads 261 and 262 for the heater which are provided on the back surface 223b of the insulating layer 223 on the base end side thereof. As viewed in the longitudinal direction from the front end side, the heat generation resistor 210 includes a heat generation portion 212 which extends in a meandering manner, a pair of heater lead portion 213, and strip-shaped electrode terminals 211 connected to end portions of the heater lead portions 213. The electrode terminals 211 are electrically connected to the pair of external connection pads 261 and 262 for the heater via conductors (not shown) formed in through-holes 223h1 and 223h2 formed in a based end portion of the insulating layer 223.

The heater 14 is used to heat the sensor element 10 (the oxygen concentration cell 12 and the oxygen pump cell 13) to an activation temperature so as to enhance oxygen-ion conductivity of the solid electrolyte layers to thereby stabilize operation.

FIG. 2 schematically shows the fractured portion F of the sensor element 10 shown in FIG. 1, which is formed at a position located rearward of the longitudinal center of the sensor element 10. However, as described above, since the first fixing member 22 presses the sensor element 10 from the outside and fixes the sensor element 10, portions of the sensor element 10 which are physically separated at the fractured portion F are in close contact with each other. Accordingly, although the paired third and fourth lead portions 143 and 144, the paired first and second lead portions 133 and 134, and the heat generation resistor 210 (the heater lead portions 213), which extend through a portion of the sensor element 10 surrounded by the first fixing member 22 are broken at the fractured portion F, the breakage of the lead portions is not noticeable, because contact (electrically continuity) between physically separated portions of each lead portion is maintained by means of pressing force (fixing force) of the first fixing member 22.

In the present embodiment, the first solid electrolyte layer 111 and the second solid electrolyte layer 121 are formed of partially stabilized zirconia (zirconia containing yttria or calcia as a stabilizer). The insulating layers 51B, 53, 221, and 223 are mainly formed of alumina. The detection electrode 131, the reference electrode 132, the third electrode 141, the fourth electrode 142, and the heat generation resistor 210 are formed of, for example, Pt.

Notably, in the case where the detection of conductor breakage according to the present invention is performed for the oxygen concentration cell 12, a combination of the detection electrode 131 and the first lead portion 133, and the reference electrode 132 and the second lead portion 134 corresponds to "the pair of conductors" in the claims; the first solid electrolyte layer 111 corresponds to the "solid electrolyte layer" in the claims associated with the conductors; and the oxygen concentration cell 12 corresponds to the "cell" in the claims.

Further, in the case where the detection of conductor breakage according to the present invention is performed for the oxygen pump cell 13, a combination of the third electrode 141 and the third lead portion 143, and the fourth electrode 142 and the fourth lead portion 144 corresponds to "the pair of conductors" in the claims; the second solid electrolyte layer 121 corresponds to the "solid electrolyte layer" in the claims associated with the conductors; and the oxygen pump cell 13 corresponds to the "cell" in the claims.

In the present embodiment, whereas the metallic shell 2 and the metallic cup 20 (each of which is a tubular metallic member) are formed of metal (e.g., SUS430), the first and second fixing members 22 and 23 are formed of powder of talc. Therefore, the rate of thermal expansion (coefficient of thermal expansion) of the first and second fixing members 22 and 23 is smaller than that of the tubular metallic members; i.e., the first and second fixing members 22 and 23 differ in rate of thermal expansion from the tubular metallic members. Further, whereas the metallic shell 2 and the metallic cup 20 (each of which is a tubular metallic member) are formed of metal, the sensor element 10 is composed of the first and second solid electrolyte layers 111 and 121 formed of zirconia, and the insulating layers 51B, 53, 221, and 223 mainly formed of alumina. Therefore, the rate of thermal expansion of the sensor element 10 (the first and second solid electrolyte layers 111 and 122, and the insulating layers 51B, 53, 221, and 223) is smaller than that of the tubular metallic members; i.e., the sensor element 10 differs in rate of thermal expansion from the tubular metallic members. Accordingly, as will be described in detail later, when the metallic shell 2 and the metallic cup 20 are heated (quick heating), the metallic shell 2 and the metallic cup 20 expand more quickly than the first and second fixing members 22 and 23 and the sensor element 10.

Next, a defect detection method for a sensor according to the embodiment of the present invention will be described, while the above-described sensor 1 is taken as an example.

The present invention is characterized by heating (quickly heating) the metallic shell 2 and the metallic cup 20 of the sensor 1. When the metallic shell 2 is heated, the metallic shell 2 and the metallic cup 20 in contact with the metallic shell 2 expand. Since the rate of thermal expansion of the metallic shell 2 and the metallic cup 20 is greater than that of the first and second fixing members 22 and 23 and that of the sensor element 10, as shown in FIG. 3, the metallic shell 2 expands outward more quickly than the first and second fixing members 22 and 23 and the sensor element 10 (indicated by "ex" in FIG. 3), whereby a gap G1 (a "difference in dimension" in the claims) is formed between the inner surface 25 of the metallic shell 2 and the outer surface of the second fixing member 23 and between the inner surface of the metallic cup 20 and the outer surface of the first fixing member 22.

Figure 4:
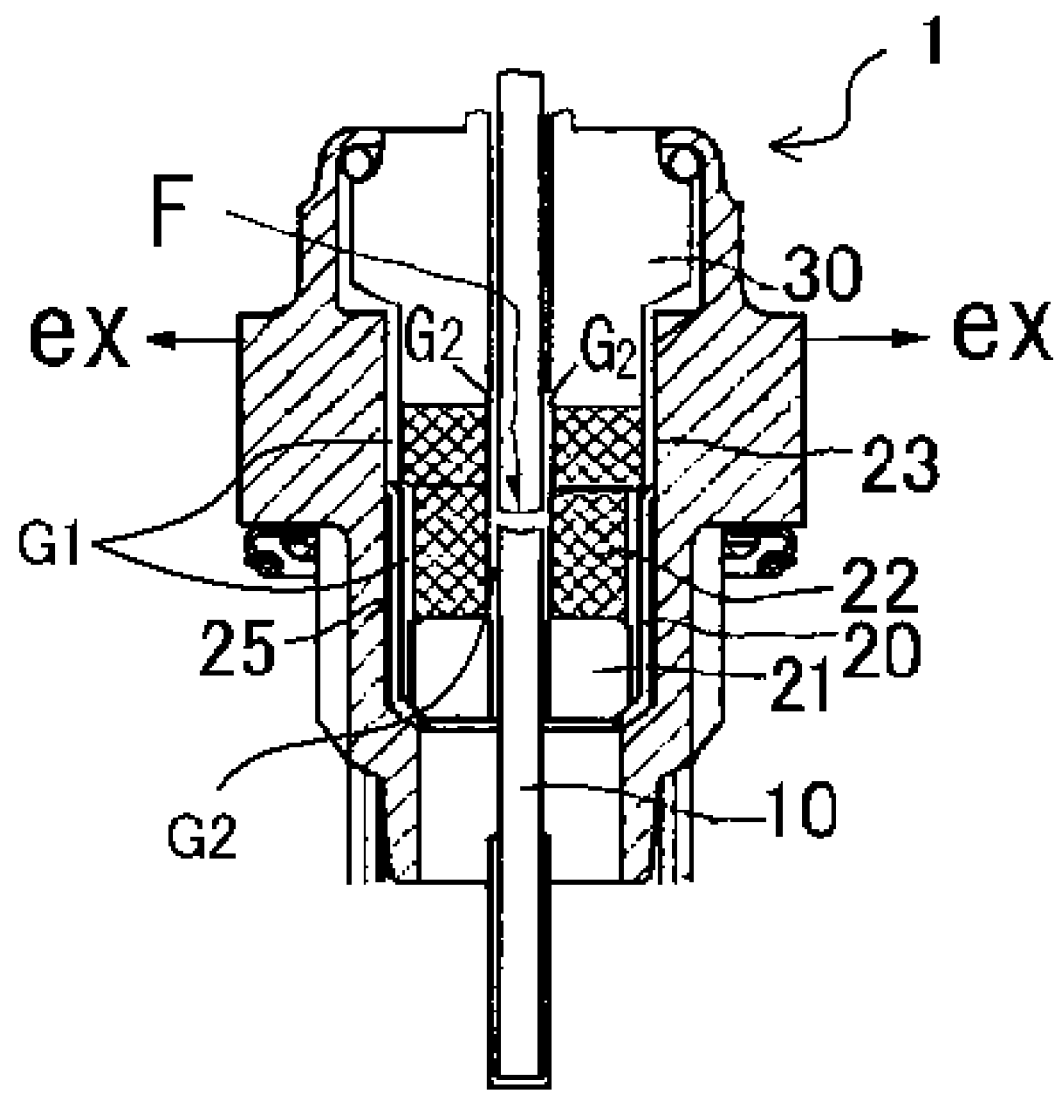
FIG. 4 is a view (cross sectional view of a main portion of the sensor 1) corresponding to FIG. 3 and showing a difference in dimension which is produced between the sensor element 10 and the fixing members 22, 23.

Thus, as shown in FIG. 4, the radial compression forces (fixing forces) of the second and first fixing members 23 and 22, which are compressively charged between the outer surface 12 of the sensor element 10 and the inner surface 25 of the metallic shell 2 and the inner surface of the metallic cup 20 such that the fixing members 23 and 22 are in contact with these surfaces, are relieved (reduced) due to generation of the gaps G1, whereby the pressing forces (fixing forces) of the first and second fixing members 22 and 23 acting on the sensor element 10 are weakened. As a result, the contact (close contact) of the first and second fixing members 22 and 23 with the sensor element 10 is broken, and a gap G2 is formed between the first fixing member 22 and the sensor element 10 and between the second fixing member 23 and the sensor element 10. In the case where a fractured portion F as shown in FIG. 1 is produced in a portion of the sensor element 10 surrounded by the first fixing member 22, because of the reduced fixing force of the first fixing member 22 (in other words, generation of the gap G2), portions of the sensor element 10 physically separated at the fractured portion F are separated further or produce a positional shift therebetween, whereby the breakage (wire breakage) of the conductors (the paired electrode lead portions 143 and 144, the paired electrode portions 133 and 134, the heat generation resistor 210 (the heater lead portions 213)) at the fractured portion F becomes noticeable. Notably, although some of the powder of talc of the first and second fixing members 22 and 23 may flow due to formation of the gap G1, this does not cause any problem in formation of the gaps G1 and G2.

Notably, in order to form the gap G2, the rate of thermal expansion of the first and second fixing members 22 and 23 must be smaller than that of the metallic shell 2 and the metallic cup 20 and the rate of thermal expansion of the sensor element 10 must be smaller than that of the metallic shell 2, because of the following reason. If the rate of thermal expansion of the sensor element 10 is equal to or greater than that of the metallic shell 2, the sensor element 10 expands quicker than the metallic shell 2 and the metallic cup 20, whereby the fixing force of the first and second fixing members 22 and 23 is not weakened, and the fractured portion F cannot be made noticeable.

Figure 3:
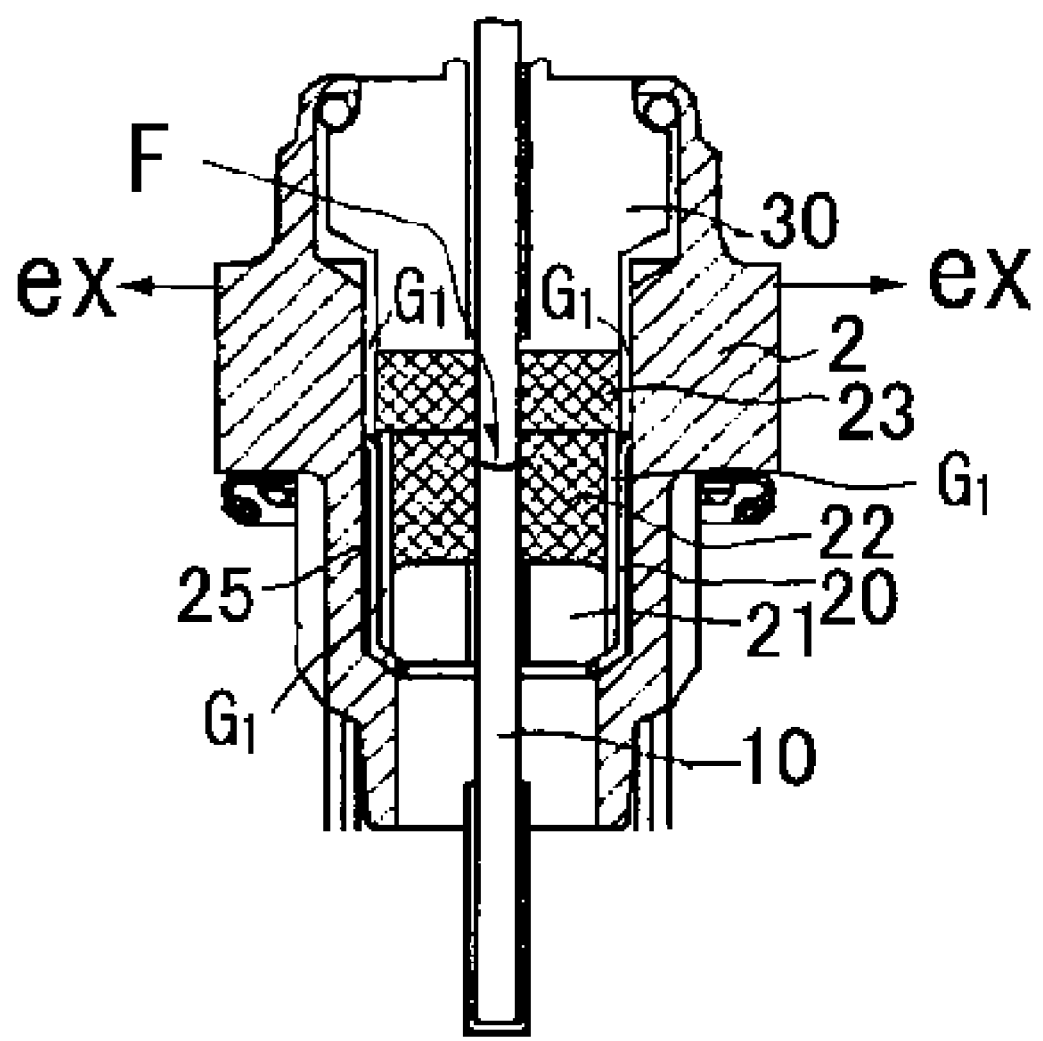
FIG. 3 is a view (cross sectional view of a main portion of the sensor 1) showing a difference in dimension which is produced between a metallic shell 2 and fixing members 22, 23 when the metallic shell 2 is heated.

Further, since each member expands three-dimensionally due to thermal expansion, in the case where a determination as to whether a difference in dimension has been produced between, for example, the sensor element 10 and the metallic shell 2 is made through visual observation, it is easy to observe dimensional changes of the sensor element 10 and the metallic shell 2 in the vertical direction of FIGS. 3 and 4 (the longitudinal direction of the sensor element 10).

Further, the expression "breakage of the sensor element 10" as used herein when describing the present invention encompasses not only the situation where the sensor element 10 is completely broken into two pieces, but also the situation where a portion of the sensor element 10 chips with resultant breakage of one of paired conductors (e.g., one of the paired third and fourth lead portions 143 and 144 or one of the paired first and second lead portions 133 and 134).

Figure 5:
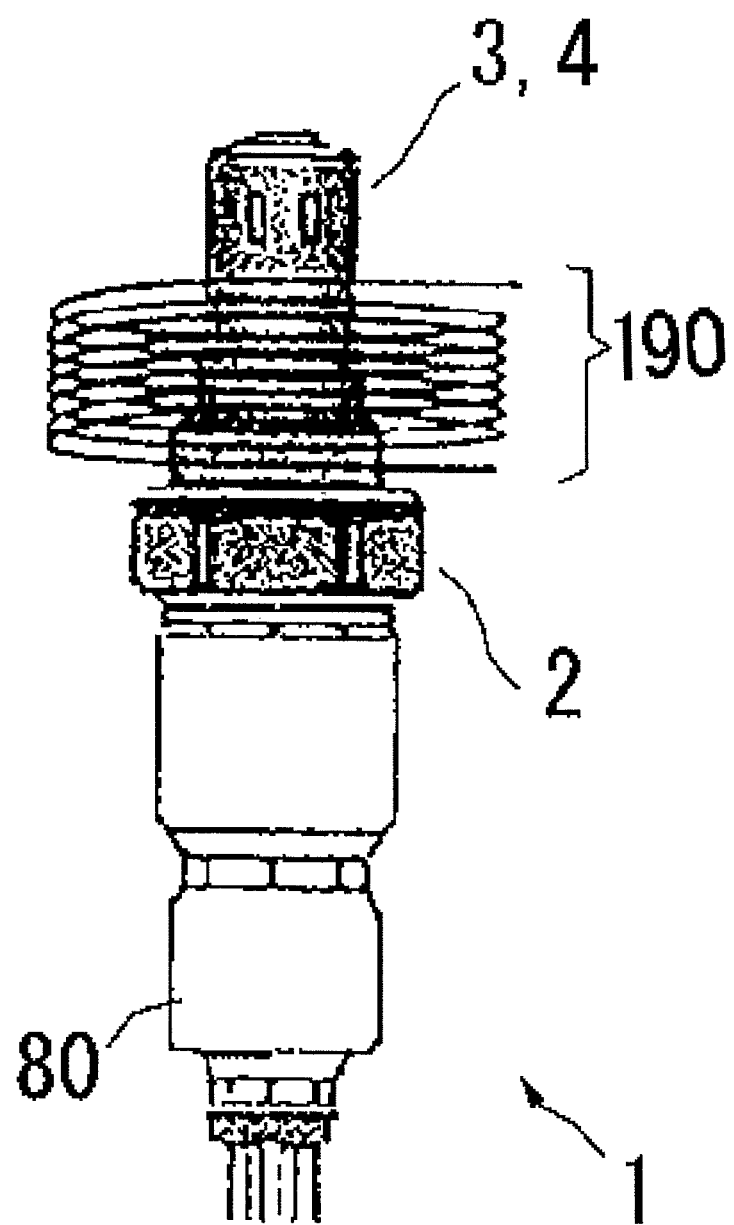
FIG. 5 is a view showing a heating apparatus used to heat the metallic shell 2 through induction heating.

FIG. 5 schematically shows a heating apparatus for heating metallic shell 2 by means of induction heating. As shown in FIG. 5, a coil 190 is disposed to surround a front end portion (on the side toward the outer and inner protectors 3 and 4) of the metallic shell 2 of the sensor 1. By means of supplying alternating current to the coil 190, the metallic shell 2, which is formed of metal, is heated. The greater the temperature rising speed of the metallic shell 2 during heating (in other words, the greater the heating speed), the greater the degree to which the expansion of the first and second fixing members 22 and 23 and the expansion of the sensor element 10 lag the expansion of the metallic shell 2, and the greater the difference in dimension G1 produced. As a result, the pressing force (fixing force) of the first and second fixing members 22 and 23 against the sensor element 10 can be weakened effectively (in other words, the gap G2 can be produced effectively). In view of the above, employment of induction heating, which can heat the metallic shell 2 quickly, is desirable.

Notably, since the metallic cup 20 is also in contact with the metallic shell 2, which is formed of the same metallic material, the metallic cup 20 is quickly heated approximately simultaneously with the metallic shell 2 when the metallic shell 2 undergoes the induction heating.

Another conceivable method of heating the metallic shell 2 other than induction heating is introduction of the metallic shell 2 into a flame. However, since a portion of the sensor 1 located rearward of the metallic shell 2 is relatively weak against heat, heating portions other than the metallic shell 2 is not preferred. In contrast, when induction heating is employed, substantially only the metallic shell 2 can be heated selectively, which is preferred.

After the metallic shell 2 is heated as described above, a determination is made as to whether or not breakage is present in paired conductors of the sensor element 10 (the third electrode 141 and the third lead portion 143, and the fourth electrode 142 and the fourth lead portion 144). Notably, in the following, a determination as to whether or not breakage is present in the paired conductors of the oxygen pump cell 13 is mainly described. However, through a similar procedure, it is possible to determine whether or not breakage is present in the paired conductors of the oxygen concentration cell 12 (the detection electrode 131 and the first lead portion 133, and the reference electrode 132 and the second lead portion 134).

Preferably, in a state where the temperature of the solid electrolyte layer (the second solid electrolyte layer 121) has been increased to an operation temperature (activation temperature) or higher, the output (voltage or current) between the paired conductors (between the third electrode 141 and the third lead portion 143, and the fourth electrode 142 and the fourth lead portion 144) is measured. Example methods of increasing the temperature of the solid electrolyte layer 121 to the operation temperature or higher include a method of heating the metallic shell 2 to a highest reaching temperature equal to or higher than the operation temperature, and a method of heating the solid electrolyte layer 121 to the operation temperature or higher by the heater 14 after completion of the heating of the metallic shell 2.

If the output (voltage or current) between the paired conductors (between the third electrode 141 and the third lead portion 143, and the fourth electrode 142 and the fourth lead portion 144) is measured in a state where the sensor element 10 has been heated to the operation temperature or higher by the heater 14 during the induction heating of the metallic shell 2, an eddy current stemming from the induction heating flows within the solid electrolyte layer (the second solid electrolyte layer 121) which has been activated (whose internal resistance has lowered), whereby the solid electrolyte layer (the second solid electrolyte layer 121) may deteriorate. Accordingly, in the case where the solid electrolyte layer (the second solid electrolyte layer 121) is heated to the operation temperature or higher through induction heating of the metallic shell 2, preferably, the output between the paired conductors (between the third electrode 141 and the third lead portion 143, and the fourth electrode 142 and the fourth lead portion 144) is measured so as to determined whether or not breakage is present, in a state where the induction heating of the metallic shell 2 is ended so as to prevent eddy current from flowing within the solid electrolyte layer (the second solid electrolyte layer 121).

Notably, as shown in FIG. 2, the sensor element 10 is configured such that the heater 14 including the heat generation resistor 210 is stacked on the sensor portion thereof. Accordingly, in addition to determining whether or not breakage is present in the paired conductors (the third electrode 141 and the third lead portion 143, and the fourth electrode 142 and the fourth lead portion 144) formed on the solid electrolyte layer (the second solid electrolyte layer 121), a determination as to whether not breakage is present in the heat generation resistor 210 may be performed so as to detect a defect of the heater 14.

Figure 6:
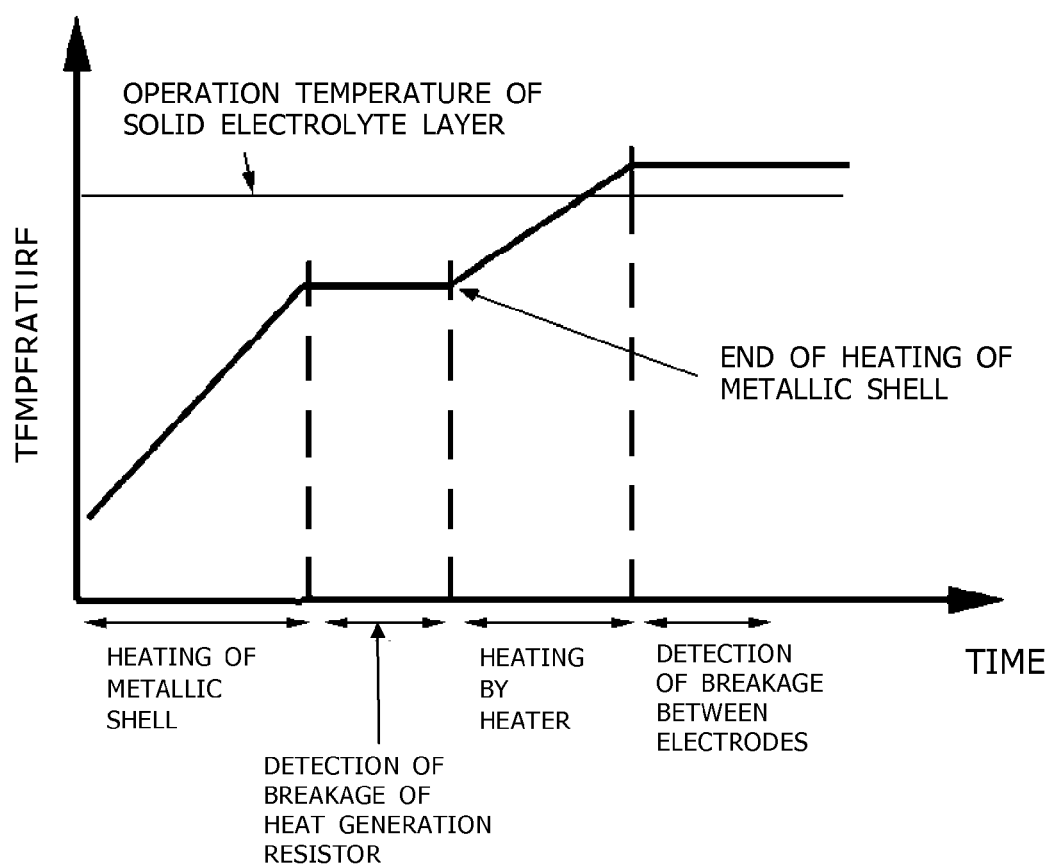
FIG. 6 is a graph showing a heating pattern according to which the temperature of the metallic shell 2 is increased.

As described above, there is another method of increasing the temperature of the solid electrolyte layer (the second solid electrolyte layer 121) to the operation temperature or higher. In this method, heating of the metallic shell 2 is stopped before the temperature of the metallic shell 2 reaches the operation temperature, and, after completion of the heating, the sensor element 10 is heated to the operation temperature or higher by the heater 14. FIG. 6 shows the heating pattern of this method.

As shown in FIG. 6, the metallic shell 2 is first heated by means of induction heating so as to produce a difference in dimension (in other words, the above-described gaps G1 and G2) attributable to the difference in rate of thermal expansion between the metallic shell 2 and the metallic cup 20 and the first and second fixing members 22 and 23 and the difference in rate of thermal expansion between the metallic shell 2 and the metallic cup 20 and the sensor element 10, and a determination as to whether or not the heat generation resistor 210 is broken is performed in a period in which the metallic shell 2 is heated (in a period in which the above-mentioned gaps G1 and G2 are produced). After completion of the heating of the metallic shell 2, within a period in which the above-mentioned gaps G1 and G2 are present (maintained) due to heat applied to the metallic shell 2 (that is, remaining or residual heat), the solid electrolyte layer (the second solid electrolyte layer 121) of the sensor element 10 is heated to the operation temperature or higher by the heater 14, and a determination is made as to whether or not breakage is present in the paired conductors (the third electrode 141 and the third lead portion 143, and the fourth electrode 142 and the fourth lead portion 144).

In the case where the heating pattern of FIG. 6 is employed, after completion of the induction heating of the metallic shell 2, the sensor element 10 (the second solid electrolyte layer 121) is heated to the operation temperature or higher through supply of electricity to the heater 14. Therefore, even though the metallic shell 2 undergoes the induction heating, it is possible to reliably prevent eddy current stemming from the induction heating from flowing within the solid electrolyte layer, to thereby prevent deterioration of the solid electrolyte layer. Notably, depending on the composition of the solid electrolyte layer, the operation temperature may be about 650° C. In such a case, once the metallic shell 2 is heated to about 500° C., the solid electrolyte layer can finally be heated to 650° C. even when the heating by the heater 14 is performed for a short period of time. Accordingly, since heating is performed by the heater 14 before the difference in dimension produced through heating of the metallic shell 2 decreases, the determination as to whether or not breakage is present in the paired conductors formed on the solid electrolyte layer can be performed sufficiently.

The present invention is not limited to the above-described embodiment, and encompasses various modifications and equivalents which fall within the scope of the present invention. For example, the sensor 1 is not limited to an oxygen sensor, and may be any sensor (an $NO_x$ sensor, an ammonia sensor, etc.) in which a sensor element which includes at least one cell having a solid electrolyte layer and a pair of electrodes is disposed within a metallic shell, and a fixing member provides a seal between the metallic shell and the sensor element.

EXAMPLE

Next, the present invention will be described in further detail by way of example; however, the present invention is not limited thereto.

Figure 7:
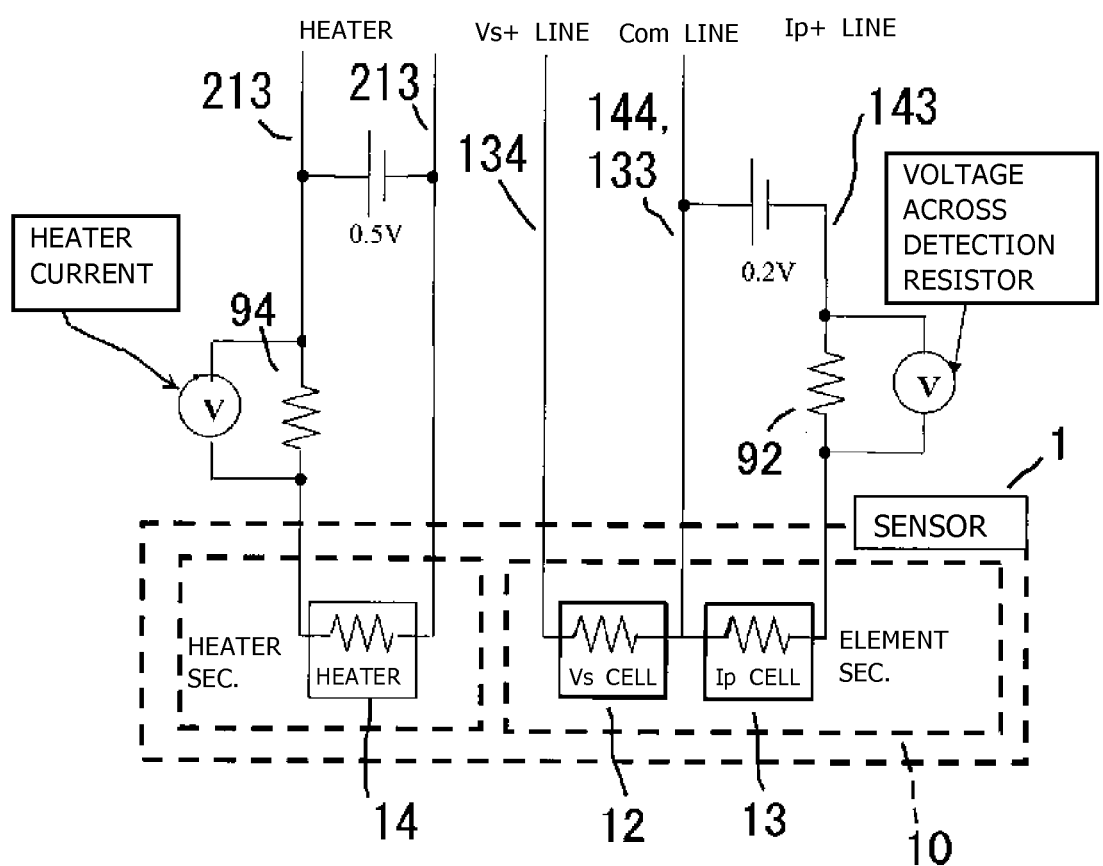
FIG. 7 is a diagram showing detection circuits for detecting breakage of a pair of conductors and breakage of a heater.

The sensor (oxygen sensor) 1 shown in FIGS. 1 and 2 was prepared. For the oxygen concentration cell (Vs cell) 12 and the oxygen pump cell (Ip cell) 13 of the sensor 1, a detection circuit as shown in FIG. 7 was provided. Specifically, a detection resistor 92 was connected to the electrode lead portion (hereinafter referred to as an "Ip+ line") 143 extending from the third electrode 141 of the Ip cell 13, and a voltage produced across the detection resistor 92 was measured. Notably, the fourth lead portion 144 and the first lead portion 133 correspond to a "Com line" of FIG. 7, and the second lead portion 134 corresponds to a "Vs+ line" of FIG. 7.

Further, a detection circuit (a detection resistor and a voltage meter for measuring a voltage produced across the detection resistor) 94 was connected to one of the heater lead portions 213, and a heater current flowing through the heater lead portion 213 was measured.

Subsequently, after the metallic shell 2 of the sensor 1 was induction-heated as shown in FIG. 5, the induction heating was stopped, and the heating was further performed by the heater 14.

Figure 8:
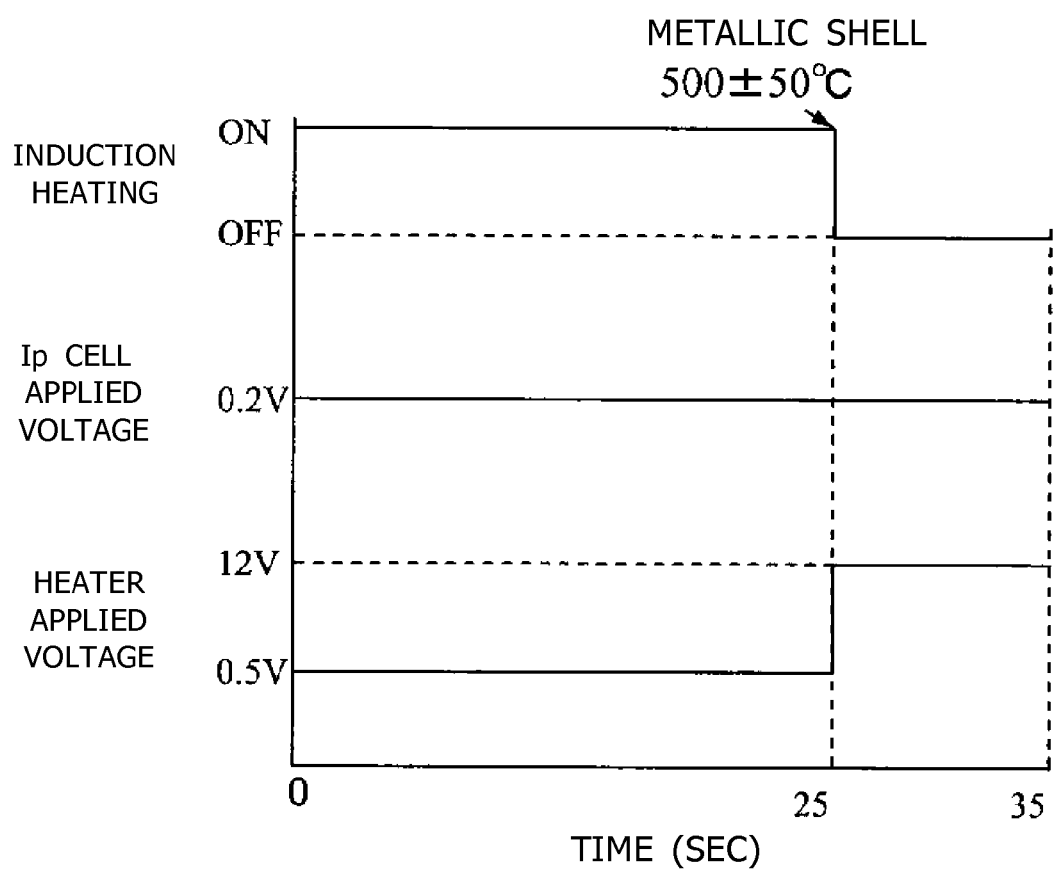
FIG. 8 is a graph showing a heating pattern in which, after completion of induction heating of the metallic shell 2, the induction heating is stopped, and heating is further performed by the heater 14.
Figure 9:
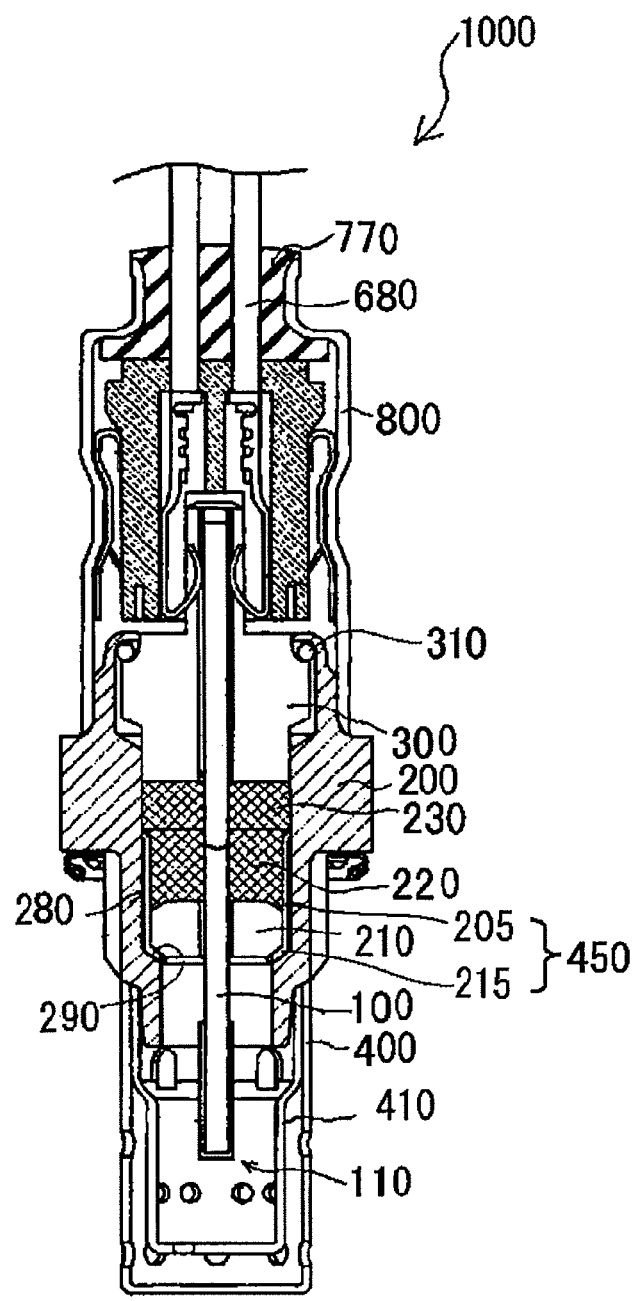
FIG. 9 is an overall cross sectional view of a conventional sensor taken along the longitudinal direction thereof.

The heating conditions are shown in FIG. 8. In a period in which the induction heating of the metallic shell 2 was being performed, a voltage of 0.5 V was applied to the heater 14 (the heat generation resistor 210), and the heater current flowing through the heat generation resistor 210 (the heater lead portions 213) was measured. Notably, after the induction heating was performed for 25 seconds, the temperature of the metallic shell 2 become 500±50° C. Next, the induction heating of the metallic shell 2 was stopped, and a voltage of 12 V was supplied to the heater 14 for 10 seconds so as to heat the sensor element 10. As a result of this heating, the temperature of the first solid electrolyte layer 121 became equal to or higher than the operation temperature (650° C.)

Then, in a state where a voltage of 0.2 V was applied between the paired conductors (between the third electrode 141 and the third lead portion 143, and the fourth electrode 142 and the fourth lead portion 144), the voltage produced across the detection resistor 92 of the IP+ line was measured. The result of the measurement shows that the voltage produced across the detection resistor 92 is about 0.2 V; i.e., that the Ip+ line is not broken.

Similarly, the heater current flowing through the detection circuit 94 of the heater lead portion 213 was measured. The result of the measurement shows that a predetermined current flows; i.e., that the heater lead portions 213 are not broken.

Meanwhile, there was prepared a sensor 1 in which the sensor element 10 was intentionally broken at a portion surrounded by the first fixing member 22 so as to fracture (break) the Ip+ line (the electrode lead portion 143) and the heater lead portions 213. Notably, in this sensor 1, in order to make the breakage of the electrode lead portion 143 and the heater lead portions 213 un-noticeable, the sensor element 10 was fixed by the first fixing member 22 in a state where portions of the sensor element 10 physically separated from each other at the fractured portion were in close contact with each other. Then, according to a procedure similar to that employed in the above-described case, after completion of induction heating of the metallic shell 2, the heating was further performed by the heater 14, and the voltage produced across the detection resistor 92 was measured. The result of the measurement shows that the voltage is 0 V; i.e., that the Ip+ line is broken.

Similarly, the heating current flowing through the detection current 94 was measured. The result of the measurement shows that no current flows; i.e., that the heater lead portions 213 are broken.

The invention claimed is:

1. A defect detection method for a sensor comprising a sensor element which includes at least one cell having a solid electrolyte layer extending in an axial direction; a tubular metallic member which surrounds the circumference of the sensor element; and a fixing member which is in contact with an inner surface of the tubular metallic member and an outer surface of the sensor element and provides a seal therebetween, the cell including a pair of conductors which are formed on the solid electrolyte layer such that the conductors extend through a portion of the sensor element surrounded by the fixing member, the method comprising the steps of:

heating the tubular metallic member so as to produce a difference in dimension attributable to a difference in rate of thermal expansion between the tubular metallic member and the fixing member and a difference in rate of thermal expansion between the tubular metallic member and the sensor element; and detecting breakage of a portion of the pair of conductors surrounded by the fixing member in a state where the difference in dimension is present.

2. The defect detection method for a sensor according to claim 1, wherein the heating is induction heating.

3. The defect detection method for a sensor according to claim 2, wherein the breakage of the pair of conductors is detected within a period which follows completion of the induction heating and in which the difference in dimension is present.

4. The defect detection method for a sensor according to any one of claims 1 to 3, wherein the sensor element is configured such that a heater including a heat generation resistor and extending in the axial direction is laminated on the cell; and the solid electrolyte layer is heated with a supply of electricity to the heat generation resistor, and the breakage of the pair of conductors is detected in a state where the solid electrolyte layer is heated.

5. The defect detection method for a sensor according to any one of claims 1 to 3, wherein the sensor element is configured such that a heater extending in the axial direction is laminated on the cell;

the heater includes a heat generation resistor extending through the portion of the sensor element surrounded by the fixing member; and the tubular metallic member is heated so as to produce the difference in dimension, and breakage of the heat generation resistor is detected in a state where the difference in dimension is present.

6. The defect detection method for a sensor according to any one of claims 1 to 3, wherein the fixing member is a compact formed through compressively charging inorganic powder between the inner surface of the tubular metallic member and the outer surface of the sensor element.

7. The defect detection method for a sensor according to claim 4, wherein the sensor element includes a heater laminated on the cell, said heater extending in the axial direction;

and having a heat generation resistor, said heat generation resistor being surrounded by the fixing member; and the tubular metallic member is heated so as to produce the difference in dimension, and breakage of the heat generation resistor is detected in a state where the difference in dimension is present.

8. The defect detection method for a sensor according to claim 4, wherein the fixing member is a compact formed through compressively charging inorganic powder between the inner surface of the tubular metallic member and the outer surface of the sensor element.

9. The defect detection method for a sensor according to claim 5, wherein the fixing member is a compact formed through compressively charging inorganic powder between the inner surface of the tubular metallic member and the outer surface of the sensor element.

* * * * *

UNITED STATES PATENT AND TRADEMARK OFFICE
CERTIFICATE OF CORRECTION

PATENT NO. : 8,513,961 B2  
APPLICATION NO. : 12/688956  
DATED : August 20, 2013  
INVENTOR(S) : Fujita et al.

Page 1 of 1

It is certified that error appears in the above-identified patent and that said Letters Patent is hereby corrected as shown below:

On Title page, Item (30), please insert:

--(30)  Foreign Application Priority Data

January 15, 2010    (JP) ................................. 2010-007731--

Signed and Sealed this  
First Day of October, 2013

Teresa Stanek Rea  
*Deputy Director of the United States Patent and Trademark Office*